United States Patent [19]

Yoneyama et al.

[11] Patent Number: 5,015,469

[45] Date of Patent: May 14, 1991

[54] WATER-IN-OIL EMULSION TYPE COSMETICS

[75] Inventors: Toshio Yoneyama; Michihiro Yamaguchi; Shinji Tobe; Tomiyuki Nanba; Masaaki Ishiwatari; Hidekazu Toyoda; Shin Nakamura; Yoshimaru Kumano; Sadaki Takata; Hiromi Ito, all of Yokohama, Japan

[73] Assignee: Shideido Company Ltd., Tokyo, Japan

[21] Appl. No.: 560,486

[22] Filed: Jul. 23, 1990

Related U.S. Application Data

[63] Continuation of Ser. No. 197,869, May 24, 1988, abandoned.

[30] Foreign Application Priority Data

Jan. 12, 1988 [JP] Japan .................................. 63-4352

[51] Int. Cl.[5] .................... A61K 7/42; A61K 7/021; B01J 13/00
[52] U.S. Cl. ........................................ 424/59; 424/63; 424/64; 514/844; 514/845; 514/846; 514/847; 514/873; 514/938; 514/941; 252/308; 252/174.15
[58] Field of Search .................... 424/59, 63, 64; 514/844, 845, 846, 847, 873, 938, 941; 252/308, 174.15

[56] References Cited

U.S. PATENT DOCUMENTS

| 3,562,786 | 2/1971 | Bailey ........................ 252/174.15 X |
| 3,933,672 | 1/1976 | Bartolotta et al. ................... 252/321 |
| 4,122,029 | 10/1978 | Gee ..................................... 252/309 |
| 4,226,736 | 10/1980 | Bush ................................ 252/174.21 |
| 4,584,125 | 4/1986 | Griswold ............................. 252/358 |
| 4,677,158 | 6/1987 | Tso et al. .......................... 252/313.2 |
| 4,793,942 | 12/1988 | Lokkesmoe et al. ........... 252/174.16 |

FOREIGN PATENT DOCUMENTS

| 0047801 | 3/1982 | European Pat. Off. . |
| 0155806 | 9/1985 | European Pat. Off. . |
| 2065687 | 7/1981 | United Kingdom . |

*Primary Examiner*—Frederick E. Waddell
*Assistant Examiner*—Catherine S. Kilby Scalzo
*Attorney, Agent, or Firm*—Sprung Horn Kramer & Woods

[57] ABSTRACT

A water-in-oil type emulsified composition containing a water-swellable clay mineral, a nonionic surfactant, an oil component, and water as the essential constituents or containing a water-swellable clay mineral, a quaternary ammonium salt type cationic surfactant, one or two more kinds of polyoxyalkylene modified organopolysiloxane, an aqueous phase, and an oil phase containing one or two or more kinds of organic silicone resin comprising the units of the formula:

$$RnSiO_{(4-n)/2}$$

wherein R is a hydrocarbon group having 1 to 6 carbon atoms or a phenyl group, and n represents a value of 1.0 to 1.8, and a water- and polyhydric alcohol-in-oil type emulsified composition containing an oil phase containing a polyoxyalkylene modified organopolysiloxane, a water-swellable clay mineral, a quaternary ammonium salt type cationic surfactant and a silicone oil, water, and a polyhydric alcohol.

6 Claims, 1 Drawing Sheet

Fig.1

WATER-IN-OIL EMULSION TYPE COSMETICS

This application is a continuation of application Ser. No. 07/197,869, filed May 24, 1988, now abandoned.

BACKGROUND OF THE INVENTION

1. Field of the Invention

The present invention relates to a water-in-oil type (hereinafter abbreviated as W/O type) emulsified composition useful as a cosmetic or ointment base. More specifically, it relates to a water-in-oil type emulsified composition having specific features whereby a range of oils from polar oils to non-polar oils can be widely employed as the oil component which becomes the outer phase and the emulsified composition obtained has an excellent temperature stability and usability.

The present invention also relates to a water-and polyhydric alcohol-in-oil type emulsified composition useful as a cosmetic or ointment base. More specifically, it relates to a water- and polyhydric alcohol-in-oil type emulsified composition having specific features whereby a silicone oil can be used as the oil component which becomes the outer phase, and the emulsified composition obtained has an excellent temperature stability. In the second aspect of the present invention, the composition is not referred to as a water-in-oil type emulsified composition or polyhydric alcohol-in-oil type emulsified composition, because the inner phase of this emulsion composition comprising the main component exists in the region bridging the region of water and the region of polyhydric alcohol, and therefore, neither expression is adequate. Accordingly, the term water- and polyhydric alcohol-in-oil type emulsified composition denotes an emulsified composition containing both water and a polyhydric alcohol in the oil phase.

2. Description of the Related Art

In the prior art, to obtain a W/O type emulsified composition, a lipophilic surfactant having a HLB value of 1 to 12, for example, a polyhydric alcohol fatty acid ester type surfactant such as glycerine fatty acid ester, sorbitan fatty acid ester, etc., is used as the emulsifier, this surfactant is added in an amount of about 0.4 to 5.0 g into the oil phase, to be dissolved therein by heating to about 70° to 80° C., and the aqueous phase heated to about the same temperature is then added, followed by stirring by a homomixer, etc., to obtain a W/O type emulsified composition (hereinafter called W/O type emulsion).

Nevertheless, the W/O type emulsion thus obtained has a drawback in that a system having an excellent temperature stability and usability can be obtained only with difficulty, compared with the oil-in-water type (hereinafter called O/W type) emulsion. For example, with regard to the temperature stability, a separation of the oil phase, which is the continuous phase, may occur due to an agglomeration of water droplets at a low temperature. This oil phase separation also occurs at a high temperature, in that water droplets are combined, and thus have an increased particle size, and precipitated to form a sediment lower layer, and thus the upper layer consists of only the oil phase. With regard to usability, since the outer phase consists of an oil component, the advantages of skin protection, flexibility, etc., can be obtained in the fields of cosmetics and pharmaceuticals, although the drawbacks of stickiness during usage and a high skin barrier also exist.

In a known method for improving the temperature stability, a large amount of a wax is formulated in the oil phase, but although low temperature stability may be improved by this method, during storage at high temperature, a softening or melting, occurs of the formulated wax, and therefore, oil phase separation caused by water droplet combination cannot be alleviated, and thus another drawback of a problem of usability, such as spreading, arises.

As a method for eliminating the such usability problems, preferably a polar oil component having ester bond, as widely employed in the O/W type emulsion system, is formulated, but when the W/O type emulsifier used in the prior art is formulated, it is difficult to form a W/O type emulsion having an excellent stability in a system wherein a polar oil component is also formulated.

SUMMARY OF THE INVENTION

Accordingly, the objects of the present invention are to eliminate the above-mentioned disadvantages of the prior art and to provide a water-in-oil type emulsified composition capable of being widely employed as an oil component and having an excellent temperature stability and usability.

Another object of the present invention is to provide a water- and polyhydric alcohol-in-oil type emulsified composition capable of being employed as an oil component and having an excellent temperature stability.

Other objects and advantages of the present invention will be apparent from the following description.

In accordance with the present invention, there is provided a water-in-oil type emulsified composition comprising, a water-swellable clay mineral, a nonionic surfactant, an oil component, and water, as the essential constituents.

In accordance with the present invention, there is also provided a water-in-oil type emulsified composition comprising, a water-swellable clay mineral, a quaternary ammonium salt type cationic surfactant, one or two or more kinds of polyoxyalkylene modified organopolysiloxane, an aqueous phase, and an oil phase containing one or two or more kinds of an organic silicone resin comprising the units of the formula:

wherein R is a hydrocarbon group having 1 to 6 carbon atoms or a phenyl group, and n represents a value of 1.0 to 1.8.

In accordance with the present invention, there is further provided a water- and polyhydric alcohol-in-oil type emulsified composition comprising an oil component containing a silicone oil using a polyoxyalkylene modified organopolysiloxane, a water-swellable clay mineral, a quaternary ammonium salt type cationic surfactant water, and a polyhydric alcohol.

BRIEF DESCRIPTION OF THE DRAWINGS

The present invention will be better understood from the description set forth below with reference to the accompanying drawing of FIG. 1, which shows the relationship between the amounts formulated and viscosity of Smectite. In FIG. 1, the axis of the ordinate represents the viscosity (cps), and the axis of the abscissa shows the % by weight of Smectite.

DESCRIPTION OF THE PREFERRED EMBODIMENTS

The water-swellable clay minerals to be used in the present invention are laminar silicate minerals belonging to genus Smectite generally including montmorillonite, beidelite, nontronite, saponite, hectorite, etc. These may be natural or synthetic. Examples of the commercially available products are Kunipia, Smecton (both from Kunipia Kogyo), Veegum (from Vanderbilt Co.), Laponite (from Laporte Co.), fluorine tetra silicic mica (from Topy Kogyo K.K.). In the practice of the present invention, one or more kinds of minerals are used from these water-swellable clay minerals. The formulated amount is suitably 0.2 to 5.0% by weight, more preferably 0.2 to 3.0% by weight, based on the total weight of the emulsified composition of the present invention. If the proportion is less than 0.2% by weight, the temperature stability may not be satisfactory, depending on the product, and if formulated in excess of 5.0% by weight, the viscosity of the system may be increased, which may have an adverse affect on the usability of some product.

As the nonionic surfactant to be used in the first aspect of the present invention, nonionic surfactants having an HLB value of 2 to 16, more preferably 3 to 12 may be included. The HLB value of the nonionic surfactant is calculated by the Kawakami formula shown below:

$$HLB = 7 + 11.7 \cdot \log \frac{Mw}{Mo}$$

(wherein Mw represents the molecular weight of the hydrophilic group portion, and Mo represents the molecular weight of the lipophilic group portion.)

Specific examples may include ethylene oxide addition type surfactants, including ether type surfactants such as polyoxyethylene 2-30 mole addition [hereinafter abbreviated as POE (2-30)]oleyl ether, POE (2-35) stearyl ether, POE (2-20) lauryl ether, POE (1-20) alkylphenyl ether, POE (6-18) behenyl ether, POE (5-25) 2-decylpentadecyl ether, POE (3-30) 2-decyltetradecyl ether, POE (8-16) 2-octyldecyl ether, etc.; ester type surfactants such as POE (4-60) hardened castor oil, POE (3-14) fatty acid monoester, POE (6-30) fatty acid diester, POE (5-20) sorbitan fatty acid ester, etc.; ether ester type surfactants such as POE (2-30) glyceryl monoisostearate, POE (10-60) glyceryl triisostearate, POE (7-50) hardened castor oil monoisostearate, POE (12-60) hardened castor oil triisostearate, etc.; and polyhydric alcohol fatty acid ester type surfactants including polyglycerine fatty acid esters such as decaglyceryl tetraoleate, hexaglyceryl triisostearate, tetraglyceryl diisostearate, diglyceryl diisostearate, etc.; glycerine fatty acid esters such as glyceryl monostearate, glyceryl monoisostearate, glyceryl monooleate, etc. Among these surfactants, nonionic surfactants such as polyglycerine fatty acid esters of triglycerine or higher such as decaglyceryl tetraoleate, hexaglyceryl triisostearate, tetraglyceryl diisostearate, POE addition ether type surfactants such as POE (2-12) oleyl ether, POE (3-12) stearyl ether, POE (2-10) lauryl ether, POE (2-10) nonylphenyl ether, POE (6-15) behenyl ether, POE (5-20) 2-decylpentadecyl ether, POE (5-17) 2-decyltetradecyl ether, and POE (8-16) 2-octyldecyl ether, etc.; POE addition ester type surfactants such as POE (10-20) hardened castor oil, POE (5-14) oleic acid monoester, POE (6-20) oleic acid diester, POE (5-10) sorbitan oleic acid ester, etc.; POE addition ether ester type surfactants such as POE (3-15) glyceryl monoisostearate, POE (10-40) glyceryl triisostearate, etc., are particularly preferred.

As another type of the nonionic surfactants to be used in the present invention, there may be included polyether modified silicone compounds represented by the following formulae. Note, these surfactants are particularly suitable when the oil is a silicone oil or an oil containing a silicone oil.

In the practice of the first aspect of the present invention, one or two or more kinds may be selected and used as desired from among these nonionic surfactants. The amount formulated is preferably 0.05 to 2-fold relative to the water-swellable clay mineral.

As the oil component to be used in the first aspect of the present invention, all of the oil components generally employed in cosmetics, pharmaceuticals, etc., can be used, and the range of from polar oils to non-polar oils can be widely used as the oil. Examples of the oil component include hydrocarbon oils such as liquid paraffin, squalane, isoparaffin, branched chain light paraffin, etc.; ester oils such as isopropyl myristate, cetyl isooctanoate, glyceryl trioctanoate, etc.; silicone oils such as octamethyltetrasiloxane, decamethylcyclopentasiloxane, dimethylpolysiloxane, methylphenylpolysiloxane, etc. Also waxes such as petrolatum, microcrystalline, lanolin, beeswax, etc., can be formulated within the range which does not impair the effect of the present invention. These oil components are formulated in amounts of about 5 to 90% by weight, preferably 10 to 80% by weight, in the W/O type emulsion.

The quaternary salt type cationic surfactant to be used in the second aspect of the present invention is represented by the following formula:

wherein $R_1$ is an alkyl group having 10 to 22 carbon atoms or a benzyl group, $R_2$ is a methyl group or an alkyl group having 10 to 22 carbon atoms, $R_3$ and $R_4$ are each an alkyl group or hydroxyalkyl group having 1 to 3 carbon atoms, and X represents a halogen atom or a methyl sulfate residue. For example, there may be included dodecyltrimethylammonium chloride, myristyltrimethylammonium chloride, cetyltrimethylammonium chloride, stearyltrimethylammonium chloride, arachyltrimethylammonium chloride, behenyltrimethylammonium chloride, myristyldimethylethylammonium chloride, cetyldimethylethylammonium chloride, stearyldimethylethylammonium chloride, arachyldimethylethylammonium chloride, behenyldimethylethylammonium chloride, myristyldiethylmethylammonium chloride, cetyldiethylmethylammonium chloride, stearyldiethylmethylammonium chloride, arachyldiethylmethylammonium chloride, behenyldiethylmethylammonium chloride, benzyldimethylmyristylammonium chloride, benzyldimethylcetylammonium chloride, benzyldimethylstearylammonium chloride, benzyldimethylbehenylammonium chloride, benzylmethylethylcetylammonium chloride, benzylmethylethylstearylammonium chloride, distearyldimethylammonium chloride, dibehenyldihydroxyethylammonium chloride, and corresponding bromides, etc., and further, dipalmitylpropylethylammonium methylsulfate, etc.

In the practice of the present invention, one or more kinds of these surfactants may be selected as desired.

The content of the quaternary ammonium salt type cationic surfactant in the W/O type emulsion of the present invention is preferably 40 to 140 milliequivalents (hereinafter abbreviated as meq) more preferably 60 to 120 meq, per 100 g of the water-swellable clay mineral. The quaternary ammonium salt type cationic surfactant and the water-swellable clay mineral may be added separately to the oil phase and the aqueous phase, respectively, during the preparation of the emulsion, or alternatively both, including a commercial product (e.g., Benton, produced by the National Lead Co.) may be previously allowed to react in a suitable solvent, and the reaction product may be added to the oil phase.

The polyoxyalkylene modified organopolysiloxane to be used in the second aspect of the present invention is preferably a polyoxyalkylene modified organopolysiloxane represented by the formulae (A), (B), (C), and (D) shown above, and any one or two or more kinds thereof may be formulated; the formulated amount being preferably 75 to 2000 g, more preferably 100 to 1500 g, based on 100 g of the water-swellable clay mineral.

The organic silicone resin to be used in the second aspect of the present invention comprises a suitable combination of the $R_3SiO_{1/2}$ units, $R_2SiO$ units, $RSiO_{3/2}$ units and $SiO_2$ units, and the proportion thereof is selected so as to satisfy the average formula: $RnSiO_{(4-n)/2}$ (R represents a hydrocarbon having 1 to 6 carbon atoms or a phenyl group, and n represents a value of 1.0 to 1.8), and desirably has an average molecular weight of about 1500 to 10000.

The amount of the organic silicone resin formulated in the present invention is 0.5 to 50% by weight in the emulsion composition, preferably 1 to 30% by weight. If less than 0.5% by weight, sufficient hardening cannot be obtained, and if over 50% by weight, the compatibility thereof with other oil components may be lowered, and the stickiness increased.

The polyoxyalkylene modified organopolysiloxane to be used in the third aspect of the present invention are those described above.

The water-swellable clay minerals to be used in the third aspect of the present invention are those as described above.

The quaternary salt type cationic surfactants to be used in the third aspect of the present invention are those as mentioned above.

The amounts of polyoxyalkylene modified organopolysiloxane, the water-swellable clay mineral, and the quaternary ammonium salt type cationic surfactant to be used in the third aspect of the present invention are controlled in accordance with the inner phase ratio and the viscosity of the emulsified composition to be obtained. Since the polyoxyalkylene modified organopolysiloxane participates in the emulsifiability, if the amount is too small, the emulsifiability is lowered, and the water-swellable clay mineral and the quaternary ammonium salt type cationic surfactant tend to raise the viscosity as the amounts formulated thereof are increased. Accordingly, the amounts of polyoxyalkylene modified organopolysiloxane, the water-swellable clay mineral and the quaternary ammonium salt type cationic surfactant formulated are preferably 0.5 to 20% by weight, 0.1 to 5% by weight, and 0.1 to 2% by weight, respectively.

As the silicone oil to be used as the oil phase in the third aspect of the present invention, any of those conventionally used for cosmetics or pharmaceuticals may be used, as exemplified by dimethylpolysiloxane, dimethylcyclopolysiloxane, methylphenylpolysiloxane, methylhydrogenpolysiloxane, higher fatty acid modified organopolysiloxane, higher alcohol modified organopolysiloxane, trimethylsiloxy silicate, etc. In particular, to remove the sticky feeling during usage, volatile dimethylpolysiloxane and dimethylcyclopolysiloxane having the structures (E) and (F) shown below can be exemplified, and one or more kinds thereof may be selected and used as desired.

The amount of the silicone oil formulated is related to the amount of the other oil phase components. If the amount of silicone oil is small, the properties of the oil phase become almost the same as the properties of the other formulated oil components, and thus a lipophilic surfactant suitable for the oil phase is preferably used. On the other hand, if the amount of silicone oil is high, the polyoxyalkylene modified organopolysiloxane of the present invention suitable for a silicone oil is preferably used. Accordingly, it is particularly preferred that the silicone oil comprise 50% or more of the oil phase component.

$i = 1-4$ $j = 0-3$

The polyhydric alcohol to be used in the third aspect of the present invention has 2 or more hydroxyl groups in the molecule, and includes, for example, liquid polyhydric alcohols such as polyethylene glycol, dipropylene glycol, 1,3-butylene glycol, propylene glycol, glycerine, etc., and solid polyhydric alcohols such as sorbitol, maltitol, etc. The mixing ratio of water and the polyhydric alcohol in the inner phase is preferably, water:polyhydric alcohol = 9:1 to 1:9, more preferably, in the region of about 2:3 to 3:2. When the oil component is silicone oil alone, a region giving a certain transparency appears, whereby a specific appearance feature can be imparted.

The total amount of water and the polyhydric alcohol formulated may be about 5 to 80% by weight in the water- and polyhydric alcohol-in-oil type emulsified composition, preferably 10 to 70% by weight.

In the W/O type emulsion according to the first aspect of the present invention, it is also possible to formulate amino acids and salts thereof, humectants, thickeners, preservatives, antioxidants, sequestering agents, UV-ray absorbers, drugs, natural extracts such as animal and vegetable extracts, pigments, dispersing agents, flavors, etc., if desired, within the range which does not impair the effect of the present invention. Examples of the above amino acids may include alanine, alginine, alginine hydrochloride, asparagine monohydrate, aspartic acid, citrulline, cysteine, cystine, glutamic acid, glutamic acid hydrochloride, glutamine, glycine, histidine, histidine hydrochloride, hydroxyproline, isoleucine, leucine, lysine, lysine hydrochloride, methionine, ornithine hydrochloride, proline, phenylalanine, serine, threonine, tryprophan, tyrosine, valine, dopa, o-aminobutyric acid, etc., which comprise a L-derivative, D-derivative, and DL-derivative. Particularly preferred among the above are glycine, L-hydroxyproline, L-alanine, L-proline, and L-serine, and the metals for forming salts therewith may include sodium, potassium, lithium, calcium, and magnesium, etc.

For preparing the water-in-oil type emulsified composition according to the first aspect of the present invention, for example, there may be included the method in which the water-swellable clay mineral, the oil component and the nonionic surfactant are mixed with stirring by heating to about 70° C., the aqueous phase is added thereto, and the mixture is stirred, or the method in which the oil component and the nonionic surfactant are mixed by heating at about 70° C., and the aqueous phase having the water-swellable clay mineral dispersed in and swelled with water is added, followed by stirring, etc.

In the W/O type emulsion according to the second aspect of the present invention, all oil components generally employed in cosmetics, pharmaceuticals, etc., other than the above oil components can be used, and a broad range of from polar oils to non-polar oils can be used. Examples of oil components may include hydrocarbon type oil components such as liquid paraffin, squalane, petrolatum, microcrystalline wax, etc.; ester oils such as isopropyl myristate, cetyl isooctanoate, glyceryl trioctanoate, etc.; silicone oils such as octamethyltetrasiloxane, decamethylpentasiloxane, dimethylpolysiloxane, methylphenylpolysiloxane, etc.; high molecular weight silicones exhibiting soft rubbery state such as dimethylpolysiloxane, methylphenylpolysiloxane, terminal hydroxyl containing dimethylpolysiloxane, terminal hydroxyl containing methylphenylpolysiloxane (i.e., dimethylpolysiloxane containing a terminal hydroxyl group), etc.; lanolin, beeswax, olive oil, coconut oil, safflower oil, castor oil, cottonseed oil, jojoba oil, carunauba wax, macademia nut oil, fatty acids, higher alcohols, etc.; and drugs such as antiphlogistics, vitamins, hormones, etc.; these oil components can be formulated within the range which does not impair the effect of the present invention. Namely, these oil components can be formulated in the amount of 5 to 90% by weight in the W/O type emulsion, preferably 10 to 80% by weight.

In the W/O type emulsion according to the second aspect of the present invention, if desired, oil-soluble and water-soluble substances or dispersible substances can be formulated within the range which does not impair the effect of the present invention. For example, amino acids and salts thereof in NMF (Natural Moisturizing Factor) existing in the stratum corneum, lower alcohols, mucopolysaccharides, humectants, thickeners, preservatives, antioxidants, sequestering agents, UV-ray absorbers, drugs, galenicals, pigments, dispersing agents, flavors, etc. can be formulated.

Also, in the emulsified composition according to the second aspect of the present invention, components conventionally used can be formulated within the range which does not impair the effect of the present invention. For example, there can be formulated in the emulsified composition; as the aqueous phase component, mucopolysaccharides such as sodium hyaluronate; organic acids and organic acid salts such as amino acids, amino acid salts, hydroxyacid salts, etc.; as the oil phase component, solid or semi-solid oil components such as petrolatum, lanolin, ceresine, silicone wax, microcrystalline wax, carunauba wax, candelilla wax, higher fatty acids, higher alcohols, etc.; fluid oil components such as squalane, liquid paraffin, ester oils, triglycerides, etc.; surfactants such as cationic surfactants, anionic surfactants, nonionic surfactants, etc.; drugs such as vitamin E, vitamin E acetate, etc.; styptics; antioxidants; preservatives; flavors; pH controllers such as sodium biphosphate, etc.; thickeners; UV-ray absorbers; inorganic powders such as talc, kaolin, mica, silica, magnesium silicate, calcium silicate, aluminium silicate, hydrous iron oxide, hydroxyapatite, etc.; organic powders such as nylon powder, polyethylene powder, benzoguanamine powder, tetrafluoroethylene powder, boron nitride, etc.; inorganic pigments such as titanium oxide, zinc oxide, iron oxide, iron titanate, yellow earth, Mango Violet, Cobalt Violet, chromium hydroxide, chromium oxide, cobalt titanate, Prussian Blue, Ultramarine, etc.; pearl pigments such as titanium oxide coated mica, titanium oxide coated talc, fish scales, etc.; tar type dyes formed into lake and natural dyes formed into lake and these inorganic powders, organic powders, inorganic pigments, organic pigments subjected to the hydrophobic treatment with silicone, and organic compounds, etc.

The W/O type emulsion according to the first aspect of the present invention is prepared by utilizing the complex W/O emulsifying action of a conventional emulsifier and a water-swellable clay mineral, and the total amount of both functioning as the W/O emulsifier may be as small as 0.25 to 5% by weight, whereby the viscosity can be controlled by controlling the formulated amount or the ratio of the inner aqueous phase without the formulation of a solidifying agent such as wax, and an oil component with a high polarity, which could be formulated only with difficulty in the prior art, can be used, and accordingly, an excellent storage stability over a wide temperature range is obtained. The W/O type emulsion of the present invention having these great advantages can be widely utilized in the wide fields of cosmetics and pharmaceuticals, etc.

In the W/O type emulsion according to the second aspect of the present invention, by utilizing an organic modified clay mineral formed from a water-swellable clay mineral, quaternary ammonium salt type cationic surfactant and a polyoxyalkylene modified organopolysiloxane as the emulsifier and gelling agent in the recipe, a good emulsifiability is exhibited even when the amount formulated is as small as 0.25 to 7% by weight, and by controlling the amount or the ratio of the inner aqueous phase or the outer oil phase, the viscosity can be controlled without formulating a large amount of a solidifying agent such as wax, etc. Also, an oil component with high polarity, which could be formulated only with difficulty in the prior art, also can be used, and thus the emulsion has an excellent stability over a wide temperature range. The use of the organic silicone resin as the oil phase component in the W/O type emulsion of the present invention, ensures that the emulsion has a good water resistance and water repellency, and therefore, is able to store a substance to be maintained on the skin for a long period such as a drug, UV-ray absorber, humectant, etc. The W/O type emulsion of the present invention having these great advantages can be widely utilized in fields such as cosmetics or pharmaceuticals, by making use of the specific features thereof.

According to the third aspect of the present invention, by controlling the amounts of the polyoxyalkylene modified organopolysiloxane, the waterswellable clay mineral and the quaternary ammonium salt type cationic surfactant or the ratio of the inner phase (aqueous phase), the viscosity can be controlled without the formulation of a solidifying agent such as wax, etc., and by using a silicone oil, which could be formulated only with difficulty in the prior art, the inner phase can be a region bridging the region with water as the main component and the region with a polyhydric alcohol as the main component, and the composition also has an excellent storage stability over a wide temperature range. Further, the emulsified composition of the present invention suffers little change in viscosity due to temperature changes and has a high water repellency when coated on the skin; different from the case when thickened with a wax, etc. The water- and polyhydric alcohol-in-oil type emulsified composition having these great advantages can be widely utilized in the fields of pharmaceuticals, cosmetics, paints, etc., by making use of the specific features thereof. For the water-swellable clay mineral and the quaternary ammonium salt type cationic surfactant in the emulsion of the present invention, an organic modified mineral clay previously treated (including commercial product) also may be employed, but if a control of the viscosity by controlling the formulation ratio of the water-swellable clay mineral and the quaternary ammonium salt type cationic surfactant is desired, the application range is broader if these components are formulated separately. The method for preparing the emulsified composition of the present invention may be practiced by previously treating the water-swellable clay mineral with the quaternary ammonium salt type cationic surfactant and then formulating the oil components to effect thickening, followed by an emulsification of water and the polyhydric alcohol therein, or alternatively by adding the water-swellable clay mineral to the water and polyhydric alcohol phase to effect swelling and dispersion, followed by an emulsification by adding a homogeneous mixture prepared previously by introducing the quaternary ammonium salt type cationic surfactant and the polyoxyalkylene modified organopolysiloxane into the oil phase.

EXAMPLES

The present invention will now be further illustrated by, but is by no means limited to, the following Examples, wherein all parts and percentages are expressed on a weight basis unless otherwise noted.

Example 1-1: Moisture cream

| (1) Squalane | 20.0 |
| --- | --- |
| (2) Cetyl isooctanoate | 8.5 |
| (3) Petrolatum | 1.5 |
| (4) POE (12) dioleate | 2.0 |
| (5) Flavor | q.s. |
| (6) Ethyl parahydroxybenzoate | 0.2 |
| (7) Sodium hyaluronate | 0.01 |
| (8) Glycerine | 10.0 |
| (9) 1,3-butylene glycol | 5.0 |
| (10) Veegam | 1.5 |
| (11) Purified water | balance |

Preparation Method

The components (1)-(6) were dispersed by mixing to prepare previously an oil phase, and a solution prepared by homogeneously dissolving the components (7) to (11) was then added gradually to the oil phase, with stirring by a disper, to obtain the desired moisture cream.

Example 1-2: Hand cream

| | | |
|---|---|---|
| (1) | Dimethylpolysiloxane (average polymerization degree = 9) | 30.0 |
| (2) | Liquid paraffin | 10.0 |
| (3) | Microcrystalline wax | 2.0 |
| (4) | Polyether modified silicone compound (having the structure of formula A, containing 20% of polyoxyethylene group and having an average molecular weight of 6000) | 3.0 |
| (5) | Butyl parahydroxybenzoate | 0.1 |
| (6) | Glycerine | 20.0 |
| (7) | Saponite | 2.0 |
| (8) | Purified water | balance |

Preparation Method

The desired hand cream was obtained similarly as in Example 1-1.

Example 1-3: Pre-make-up cream

| | | |
|---|---|---|
| (1) | Squalane | 23.0 |
| (2) | Decamethylcyclopentasiloxane | 5.0 |
| (3) | Microcrystalline wax | 2.0 |
| (4) | Polyether modified silicone compound (having the structure of formula A, containing 20% of the polyoxyethylene group and having an average molecular weight of 6000) | 1.0 |
| (5) | Diglyceryl diisostearate | 1.0 |
| (6) | Butyl parahydroxybenzoate | 0.1 |
| (7) | Flavor | q.s. |
| (8) | Titanium oxide | 1.0 |
| (9) | Colored pigment | 0.1 |
| (10) | Dipropylene glycol | 5.0 |
| (11) | Kunipia | 2.5 |
| (12) | Purified water | balance |

Preparation Method

The desired cosmetic base cream was obtained as in Example 1-1.

The results of tests of the viscosity and stability of Examples 1-1 to 1-3 are shown in the following table.

| Test items Sample | 0° C. Viscosity cps | 0° C. Stability | 25° C. Viscosity cps | 25° C. Stability | 50° C. Viscosity cps | 50° C. Stability |
|---|---|---|---|---|---|---|
| Example 1-1 | 320 | + | 280 | + | 200 | + |
| Example 1-2 | 280 | + | 240 | + | 180 | + |
| Example 1-3 | 470 | + | 410 | + | 360 | + |

Viscosity: measured by a cone plate type viscometer at a shear rate of 1700 sec$^{-1}$
Stability:
+: no separation observed
±: some separation of liquid phase (oil phase or aqueous phase) observed
−: remarkable separation of liquid phase observed

Example 2-1: Hand cream

| | | |
|---|---|---|
| (1) | Decamethylcyclopentasiloxane | 12.0 |
| (2) | Liquid paraffin | 10.0 |
| (3) | Organic silicone resin (average formula: $(CH_3)_{1.60}SiO_{1.20}$ molecular weight: about 3000) | 5.0 |
| (4) | Polyoxyalkylene modified organopolysiloxane*[1] | 4.0 |
| (5) | Distearyldimethylammonium chloride | 0.8 |
| (6) | Vitamin E acetate | 0.1 |
| (7) | Ethylparahydroxybenzoate | q.s. |
| (8) | Flavor | q.s. |
| (9) | Purified water | 55.7 |
| (10) | Polyethylene glycol 4000 | 1.0 |
| (11) | Glycerine | 10.0 |
| (12) | Smecton | 1.2 |

*[1] In formula (A), the average molecular weight is 6000, R is methyl group, R' is hydrogen, $p = 3$, $y = 0$, and $x = 28$.

Preparation Method

The components (1)–(8) were dissolved by mixing under heating at 70° C. to prepare an oil phase. Next, the components (9)–(12) were dispersed and mixed at 70° C. and then the mixture was gradually added, while stirring by a disper until mixed homogeneously, followed by cooling to obtain the desired hand cream.

Example 2-2: Milky lotion

| | | |
|---|---|---|
| (1) | Squalane | 13.0 |
| (2) | Petrolatum | 3.0 |
| (3) | Dimethylpolysiloxane (5 cs) | 30.0 |
| (4) | Organic silicone resin (average formula: $(CH_3)_{1.8}SiO_{1.1}$ molecular weight: about 5000) | 2.0 |
| (5) | Polyoxyalkylene modified organopolysiloxane*[2] | 2.5 |
| (6) | Behenyltrimethylammonium chloride | 0.2 |
| (7) | Ethylparahydroxybenzoate | q.s. |
| (8) | Flavor | q.s. |
| (9) | Purified water | 42.2 |
| (10) | Sodium 2-hydroxy-4-methoxybenzophenone-5-sulfonate | 0.2 |
| (11) | Polyethylene glycol 6000 | 1.0 |
| (12) | Dishcloth gourd extract | 0.5 |
| (13) | Sodium hyaluronate | 0.1 |
| (14) | 1,3-Butylene glycol | 5.0 |
| (15) | Smecton | |

*[2] In formula (B), the average molecular weight is 12000, R is methyl group, R' is hydrogen, $p = 3$, $y = 0$, and $x = 32$.

Preparation Method

The desired emulsion was obtained as in Example 2-1.

Example 2-3: Pre-make-up milky lotion

| | | |
|---|---|---|
| (1) | Squalane | 23.0 |
| (2) | Jojoba oil | 5.0 |
| (3) | Decamethylcyclopentasiloxane | 20.0 |
| (4) | Dimethylpolysiloxane (5 cs) | 20.0 |
| (5) | 2-Ethylhexyl-p-dimethylaminobenzoate | 2.0 |
| (6) | Organic silicone resin (average formula: $(CH_3)_{0.30}(C_6H_5)_{0.85}SiO_{1.43}$, molecular weight: about 8000) | 1.0 |
| (7) | Polyoxyalkylene modified organopolysiloxane*[3] | 2.0 |
| (8) | Organic modified clay mineral (obtained by reacting smecton and distearyldimethylammonium chloride at a ratio of 65:35 in water) | 1.0 |
| (9) | Flavor | q.s. |
| (10) | Purified water | 16.9 |
| (11) | Polyethylene glycol 20000 | 1.0 |
| (12) | Titanium oxide | 1.0 |
| (13) | Colored pigment | 0.1 |
| (14) | Dipropylene glycol | 7.0 |

*[3] In formula (C), the average molecular weight is 9000, R is a methyl group, R' is hydrogen, $p = 3$, $y = 0$, and $x = 25$.

Preparation Method

The desired pre-make-up milky lotion was obtained as in Example 2-2.

Example 2-4: Sun screen cream

| | | |
|---|---|---|
| (1) | 2-Ethylhexyl-p-dimethylaminobenzoate | 5.0 |
| (2) | 4-Tert-butyl-4'-methoxydibenzoyl-methane | 2.0 |
| (3) | Glyceryl Di-p-methoxysuccinate monoethylhexanoate | 2.0 |
| (4) | Petrolatum | 2.0 |
| (5) | Organic silicone resin (average formula: $(CH_3)_{1.33}SiO_{1.34}$ molecular weight: about 3000) | 15.0 |
| (6) | Decamethylcyclopentasiloxane | 21.0 |
| (7) | Dimethylpolysiloxane (molecular weight: about 300000) | 8.0 |
| (8) | Polyoxyalkylene modified organopolysiloxane*4 | 3.5 |
| (9) | 2-Hydroxy-4-methoxybenzophenone | 1.0 |
| (10) | Distearyldimethylammonium chloride | 1.2 |
| (11) | Flavor | q.s. |
| (12) | Purified water | 20.0 |
| (13) | Fine particulate titanium oxide (maximum particle size: $0.1\mu$ or less average particle size: 10 to 40 m$\mu$) | 7.0 |
| (14) | Colored pigment | 0.5 |
| (15) | Glycerine | 5.0 |
| (16) | 1,3-Butylene glycol | 5.0 |
| (17) | Veegam | 1.8 |

*4 In formula (D), the average molecular weight is 15000, R is a methyl group, R' is hydrogen, $\underline{p} = 3$, $\underline{y} = 0$, and $\underline{x} = 34$.

Preparation Method

The desired sun screen cream was obtained as in Example 2-1.

Comparative Example 2-1

This cream was obtained by replacing all of the amounts of the polyoxyalkylene modified organopolysiloxane, distearyldimethylammonium chloride, and smecton forming the organic modified clay mineral with sorbitan sesquioleate in the recipe in Example 2-1.

Comparative Example 2-2

This cream was obtained by replacing all of the amount of the polyoxyalkylene modified organopolysiloxane with diglyceryl diisostearate in Example 2-1.

Comparative Example 2-3

This cream was obtained by replacing all of the amount of the organic silicone resin with decamethylcyclopentasiloxane in Example 4.

The properties, stabilities after standing at 0° C., room temperature, and 50° C. for one month, and the functions of the W/O type emulsions in Examples 2-1, 2-4 and Comparative Examples 2-1 to 2-3 are shown in Tables 1 and 2.

The test and evaluation methods are shown below.

Stability
+: no separation observed
±: slight oil separation observed
−: remarkable oil separation observed.

Water Repellency (1) The water repellency during emulsion coating was evaluated organoleptically.
+: very good
±: average
−: poor (2) The contact angle was measured immediately after gently placing 3 $\mu$l of water droplets on thin membrane of cream (emulsion).

Residual Percentage of UV-Ray Absorber

Each of the emulsions of Example 2-4 and Comparative Example 2-3 was applied, and after swimming for 2 hours, the absorber was extracted with ethanol from the coated portion and measured by a spectrophotometer, and the residual percentage calculated by the ratio thereof before and after coating.

TABLE 1

| | Stability | | | Water repellency (organoleptic) | Contact angle |
|---|---|---|---|---|---|
| | 0° C. | RT | 50° C. | | |
| Example 2-1 | + | + | + | + | 90° |
| Comparative Example 2-1 | − | − | − | − | 50° |
| Comparative Example 2-2 | + | ± | − | − | 60° |
| Example 2-4 | + | + | + | + | 95° |
| Comparative Example 2-3 | + | + | + | ± | 70° |

TABLE 2

| | Residual percentage of UV-rays after coating of emulsion and swimming |
|---|---|
| Example 2-4 | 95% |
| Comparative Example 2-3 | 55% |

As apparent from Table 1 and Table 2, the Examples of the present invention has an excellent stability and water repellency, and the residual percentage of UV-rays absorber after swimming is high.

Example 2-5: Foundation

| | | |
|---|---|---|
| (1) | Liquid paraffin | 20.0 |
| (2) | Petrolatum | 2.0 |
| (3) | Microcrystalline wax | 1.0 |
| (4) | Glyceryl Di-p-methoxysuccinate monoethylhexanoate | 2.0 |
| (5) | 4-Tert-butyl-4'-methoxydibenzoyl-methane | 1.0 |
| (6) | Decamethylcyclopentasiloxane | 20.0 |
| (7) | Organic silicone resin (average formula: $(CH_3)_{1.23}(C_6H_5)_{0.18}SiO_{1.3}$, molecular weight: about 2000) | 8.0 |
| (8) | Polyoxyalkylene modified organopolysiloxane (using 1.0 of *1 and 0.5 of *3) | 1.5 |
| (9) | Diglyceryl diisostearate | 0.5 |
| (10) | Benton (the reaction product of a water-swellable clay mineral and a quaternary ammonium salt type cationic surfactant at 65:35) | 2.0 |
| (11) | Flavor | q.s. |
| (12) | Purified water | 13.0 |
| (13) | Glycerine | 3.0 |
| (14) | Dispersing agent | q.s. |
| (15) | Titanium oxide | 15.5 |
| (16) | Kaolin | 5.0 |
| (17) | Talc | 3.0 |
| (18) | Colored pigment | 1.0 |
| (19) | Fine particulate titanium oxide (maximum particle size: $0.1\mu$ or less average particle size: 10 to 40 m$\mu$) | 2.0 |

Preparation Method

The desired foundation was obtained as in Example 2-1.

Example 2-6: Moisture cream

| | | |
|---|---|---|
| (1) | Squalane | 2.0 |
| (2) | Cetyl isooctanoate | 2.0 |
| (3) | Octamethyltetrasiloxane | 4.0 |
| (4) | Organic silicone resin (average formula: $(CH_3)_{1.23}(C_6H_5)_{0.18}SiO_{1.30}$, molecular weight: about 2000) | 10.0 |
| (5) | Polyoxyalkylene modified organopolysiloxane (using 2.0 of *2 and 1.5 of *4) | 3.5 |
| (6) | Behenyldiethylmethylammonium chloride | 0.5 |
| (7) | Purified water | 56.5 |
| (8) | Glycerine | 15.0 |
| (9) | 1,3-Butylene glycol | 5.0 |
| (10) | Sodium glutamnate | 0.5 |
| (11) | Kunipia | 1.0 |

Preparation Method

The desired moisture cream was obtained as in Example 2-1.

Examples 2-5 and 2-6 were found to have an excellent temperature stability and usability.

Example 3-1

| | | |
|---|---|---|
| (1) | Polyoxyalkylene modified organopolysiloxane*1 | 2.0 |
| (2) | Smectite | 1.5 |
| (3) | Distearyldimethylammonium chloride | 0.5 |
| (4) | Octamethyltetracyclosiloxane | 20.0 |
|     | Dimethylpolysiloxane (6 cs) | 7.5 |
|     | Ethylparahydroxybenzoate | 0.2 |
| (5) | Purified water | 33.8 |
|     | Glycerine | 33.8 |
|     | Polyethylene glycol 6000 | 1.0 |

*1 In formula (A), the average molecular weight is 6000, the polyoxyalkylene content is 20%, R is a methyl group, R' is hydrogen, $p = 3$ and $y = 0$.

After the water-swellable clay mineral of (2) was swollen by mixing (2) and (5), the mixture was emulsified by adding a solution obtained by mixing (1), (3) and (4), and heating. The mixture was then cooled to room temperature to obtain an emulsified composition.

The following Examples and Comparative Examples were prepared according to the same method as used in Example 3-1.

| Comparative Example 3-1 | |
|---|---|
| Diglyceryl diisostearate | 2.0 |
| Smectite | 1.5 |
| Distearyldimethylammonium chloride | 0.5 |
| Octamethyltetracyclosiloxane | 20.0 |
| Dimethylpolysiloxane (6 cs) | 7.5 |
| Ethylparahydroxybenzoate | 0.2 |
| Purified water | 33.8 |
| Glycerine | 33.8 |
| Polyethylene glycol 6000 | 1.0 |
| Comparative Example 3-2 | |
| Polyoxyalkylene modified organopolysiloxane*1 | 2.0 |
| Smectite | 1.5 |
| Octamethyltetracyclosiloxane | 20.0 |
| Dimethylpolysiloxane (6 cs) | 7.5 |
| Ethylparahydroxybenzoate | 0.2 |
| Purified water | 33.8 |
| Glycerine | 33.8 |
| Polyethylene glycol 6000 | 1.0 |
| Comparative Example 3-3 | |
| Polyoxyalkylene modified organopolysiloxane*1 | 2.0 |
| Dimethyldistearylammonium chloride | 0.5 |
| Octamethyltetracyclosiloxane | 20.0 |
| Dimethylpolysiloxane (6 cs) | 7.5 |
| Ethylparahydroxybenzoate | 0.2 |
| Purified water | 33.8 |
| Glycerine | 33.8 |
| Polyethylene glycol 6000 | 1.0 |
| Comparative Example 3-4 | |
| Polyoxyalkylene modified organopolysiloxane*1 | 2.0 |
| Smectite | 1.5 |
| Distearyldimethylammonium chloride | 0.5 |
| Liquid paraffin (120 cs) | 27.5 |
| Ethylparahydroxybenzoate | 0.2 |
| Purified water | 33.8 |
| Glycerine | 33.8 |
| Polyethylene glycol 6000 | 1.0 |
| Comparative Example 3-5 | |
| Sorbitan monooleate | 2.0 |
| Liquid paraffin (120 cs) | 27.2 |
| Microcrystalline wax | 2.0 |
| Ethylparahydroxybenzoate | 0.2 |
| Purified water | 33.8 |
| Glycerine | 33.8 |
| Polyethylene glycol 6000 | 1.0 |

TABLE 3

| | | Example 3-1 | Comparative Example 3-1 | Comparative Example 3-2 | Comparative Example 3-3 | Comparative Example 3-4 | Comparative Example 3-5 |
|---|---|---|---|---|---|---|---|
| Stability | 0° C. | + | − Separated | + | + | − Separated | ± |
| | Room temperature | + | − Separated | + | + | − Separated | ± |
| | 50° C. | + | − Separated | − Separated | ± | − Separated | − Separated |
| Viscosity | cps | 100,000 or more | — | 600 | 1970 | — | 400 |

As apparent from Table 3, the water- and polyhydric alcohol-in-oil type emulsified composition of the present invention is given an excellent stability by emulsifying well water and polyhydric alcohol with a silicone oil.

Next, the amount of Smectite in Example 3-1 was reduced from 1.5% to 1.0%, 0.5%, and 0.25%, to produce Examples 3-2, 3-3 and 3-4, and Comparative Example 3-6 contained no Smectite. The relationships of the amounts with the viscosity in these Examples are shown in FIG. 1.

Figure 1:
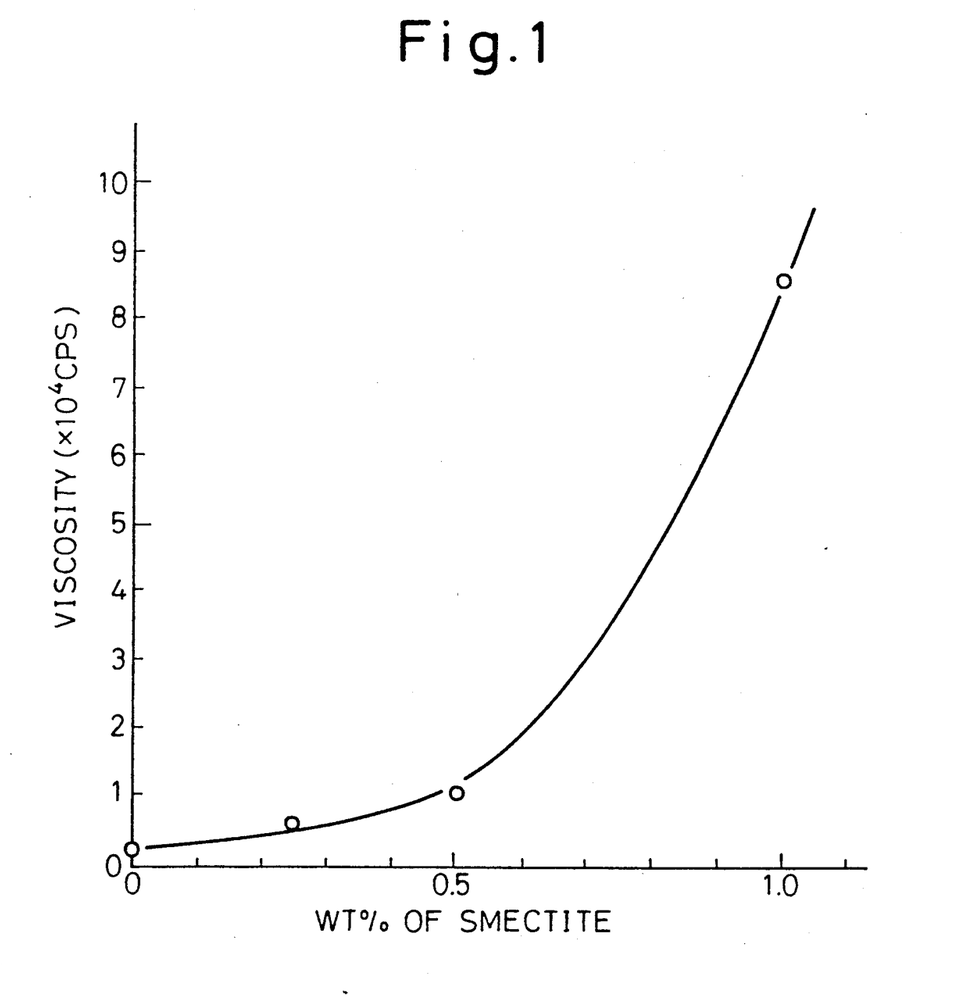

As apparent from FIG. 1, it is possible to obtain water- and polyhydric alcohol-in-oil type emulsified compositions with a desired viscosity by controlling the formulated amount of the water-swellable clay mineral.

Examples 3-5 to 3-8 and Comparative Examples 3-7 and 3-8 are shown in Table 4, and Examples 3-9 to 3-12 and Comparative Example 3-9 are shown in Table 5.

TABLE 4

| Recipe | | | | Comparative Example 3-7 | Example 3-5 | Example 3-6 | Example 3-7 | Example 3-8 | Comparative Example 3-8 |
|---|---|---|---|---|---|---|---|---|---|
| Polyoxyalkylene modified organopolysiloxane of the formula 1 (R is methyl, R' is hydrogen, p = 3, y = 0) | | | | | | | | | |
| Polyoxyalkylene group | 5%, | Average molecular weight | 3000 | 5.0 | — | — | — | — | — |
| Polyoxyalkylene group | 10%, | Average molecular weight | 3000 | — | 5.0 | — | — | — | — |
| Polyoxyalkylene group | 15%, | Average molecular weight | 3000 | — | — | 5.0 | — | — | — |
| Polyoxyalkylene group | 20%, | Average molecular weight | 3000 | — | — | — | 5.0 | — | — |
| Polyoxyalkylene group | 30%, | Average molecular weight | 3000 | — | — | — | — | 5.0 | — |
| Polyoxyalkylene group | 45%, | Average molecular weight | 3000 | — | — | — | — | — | 5.0 |
| Decamethylcyclopentasiloxane | | | | 25.0 | same as on left | same as on left | same as on left | same as on left | same as on left |
| Distearyldimethylammonium chloride | | | | 0.5 | same as on left | same as on left | same as on left | same as on left | same as on left |
| Purified water | | | | 34.0 | same as on left | same as on left | same as on left | same as on left | same as on left |
| Glycerine | | | | 34.0 | same as on left | same as on left | same as on left | same as on left | same as on left |
| Smectite | | | | 1.5 | same as on left | same as on left | same as on left | same as on left | same as on left |
| Methylparahydroxybenzoate | | | | q.s. | same as on left | same as on left | same as on left | same as on left | same as on left |
| Evaluation results | Stability | 0° C. | | ± | + | + | + | + | — |
| | | Room temperature | | ± | + | + | + | + | — |
| | | 37° C. | | — | ± | + | + | + | — |

TABLE 5

| Recipe | | | | Comparative Example 3-9 | Example 3-9 | Example 3-10 | Example 3-11 | Example 3-12 |
|---|---|---|---|---|---|---|---|---|
| Polyoxyalkylene modified organopolysiloxane of the formula 1 (R is methyl, R' is hydrogen, p = 3, y = 0) | | | | | | | | |
| Polyoxyalkylene group | 15%, | Average molecular weight | 500 | 5.0 | — | — | — | — |
| Polyoxyalkylene group | 15%, | Average molecular weight | 2000 | — | 5.0 | — | — | — |
| Polyoxyalkylene group | 15%, | Average molecular weight | 6000 | — | — | 5.0 | — | — |
| Polyoxyalkylene group | 15%, | Average molecular weight | 9000 | — | — | — | 5.0 | — |
| Polyoxyalkylene group | 15%, | Average molecular weight | 15000 | — | — | — | — | 5.0 |
| Decamethylcyclopentasiloxane | | | | 25.0 | same as on left | same as on left | same as on left | same as on left |
| Distearyldimethylammonium chloride | | | | 0.5 | same as on left | same as on left | same as on left | same as on left |
| Purified water | | | | 34.0 | same as on left | same as on left | same as on left | same as on left |
| Glycerine | | | | 34.0 | same as on left | same as on left | same as on left | same as on left |
| Smectite | | | | 1.5 | same as on left | same as on left | same as on left | same as on left |
| Methylparahydroxybenzoate | | | | q.s. | same as on left | same as on left | same as on left | same as on left |
| Evaluation results | Stability | 0° C. | | — | + | + | + | + |
| | | Room temperature | | — | + | + | + | + |
| | | 37° C. | | — | + | + | + | + |

Example 3-13

| | |
|---|---|
| Polyoxyalkylene modified organopolysiloxane*2 | 4.0 |
| Veegam | 1.0 |
| Phenyldimethylstearylammonium chloride | 0.5 |
| Octamethyltetracyclosiloxane | 20.0 |
| Trimethylsiloxy silicate | 10.0 |
| Cetyl isooctanoate | 7.5 |

-continued

| | |
|---|---|
| Ethylparahydroxybenzoate | 0.2 |
| Purified water | 5.8 |
| 1,3-butylene glycol | 50.0 |
| Polyethylene glycol 6000 | 1.0 |

*2In formula (B), the average molecular weight is 12000, the polyoxyalkylene content is 35%, R is a methyl group, R' is hydrogen, p = 3 and y = 0.

Example 3-14

| Polyoxyalkylene modified organopolysiloxane*³ | 4.0 |
|---|---|
| Saponite | 1.5 |
| Phenyldimethylstearylammonium chloride | 1.0 |
| Octamethyltetracyclosiloxane | 20.0 |
| Glyceryl isooctanoate | 10.0 |
| Ethylparahydroxybenzoate | 0.2 |
| Purified water | 43.3 |
| Dipropylene glycol | 10.0 |
| Maltitol | 10.0 |

*³In formula (C), the polyoxyalkylene content is 25%, the average molecular weight is 9000. R is a methyl group, R' is hydrogen, $p = 3$ and $y = 0$.

Example 3-15

| Polyoxyalkylene modified organopolysiloxane*⁴ | 3.0 |
|---|---|
| Smectite | 1.0 |
| Distearyldimethylammonium chloride | 0.5 |
| Octamethyltetracyclosiloxane | 30.0 |
| Dimethylpolysiloxane (6 cs) | 7.5 |
| Ethylparahydroxybenzoate | 0.2 |
| Purified water | 16.8 |
| Glycerine | 30.0 |
| Polyethylene glycol 6000 | 1.0 |
| Combined pigment (subjected to hydrophobic treatment) | 20.0 |

*⁴In formula (A), the average molecular weight is 6000, the polyoxyalkylene content is 20%, R is a methyl group, R' is hydrogen, $p = 3$ and $y = 0$.

Example 3-16

| Polyoxyalkylene modified organopolysiloxane*⁵ | 3.0 |
|---|---|
| Laponite | 1.0 |
| Distearyldimethylammonium chloride | 0.5 |
| Octamethyltetracyclosiloxane | 20.0 |
| Dimethylpolysiloxane (20 cs) | 4.5 |
| Squalane | 3.0 |
| Ethylparahydrobenzoate | 0.2 |
| Purified water | 14.0 |
| Glycerine | 53.8 |
| Sodium hyaluronate | 1.0 |

*⁵In formula (C), the average molecular weight is 9000, the polyoxyalkylene content is 25%, R is a methyl group, R' is hydrogen, $p = 3$ and $y = 0$.

Example 3-17; Cream

| | | |
|---|---|---|
| (A) | 1. Purified water | balance |
| | 2. Glycerine | 20.0 |
| | 3. L-Serin | 0.1 |
| | 4. Hyaluronic acid | 0.15 |
| | 5. Placents extract | 0.5 |
| (B) | 6. Petrolatum | 3.0 |
| | 7. Isopropyl myristate | 3.0 |
| | 8. Liquid paraffin | 5.0 |
| | 9. Dimethylpolysiloxane | 7.0 |
| | 10. Decamethyl pentasiloxane | 10.0 |
| | 11. Evening primrose oil | 0.5 |
| | 12. Cholesteryl 12-hydroxystearate | 0.5 |
| | 13. Tocopherol acetate | 0.2 |
| | 14. Polyoxyethylene modified organopolysiloxane | 3.0 |
| | 15. Cationically modified hydrophillic clay mineral | 2.0 |
| | 16. Ethylparaben | q.s. |
| | 17. Flavor | q.s. |

Preparation Method

Oil portion (B) was uniformly dispersed at 70° C. followed by gradually adding the uniformly dissolved aqueous phase (A) thereto, and then the desired cream was obtained by cooling.

We claim:

1. A water-in-oil type emulsified cosmetic composition comprising:
   (a) 0.2% to 5.5% by weight of a water-swellable clay mineral,
   (b) 40 to 140 meq per 100 g of said clay mineral of a quaternary ammonium salt cationic surfactant,
   (c) 0.05 to 2-fold relative to said clay mineral of at least one polyoxyalkylene modified organopolysiloxane,
   (d) a balance of an aqueous phase, and
   (e) 10 to 18% by weight of an oil phase containing at least one organic silicone resin comprising units of the formula:

$$RnSiO_{(4-n)/2}$$

wherein R is a hydrocarbon group having 1 to 6 carbon atoms or a phenyl group, and n represents a value of 1.0 to 1.8.

2. A water-in-oil type emulsified cosmetic composition as claimed in claim 1 wherein the aqueous phase comprises water and a polyhydric alcohol being 9:1 to 1:9.

3. A water-in-oil type emulsified cosmetic composition as claimed in claim 2, wherein the polyoxyalkylene modified organopolysiloxane in the emulsified composition is 0.5 to 10% by weight, the water-swellable clay mineral is 0.1 to 5% by weight and the quaternary ammonium salt cationic surfactant is 1 to 2% by weight.

4. A water-in-oil type emulsified cosmetic composition as claimed in claim 2, wherein the silicone oil content in the oil phase containing silicone oil is 50% by weight or more.

5. A water-in-oil type emulsified cosmetic composition as claimed in claim 2, wherein the total amount of water and the polyhydric alcohol is 5 to 80% by weight.

6. A water-in-oil type emulsified cosmetic composition as claimed in claim 1, wherein the polyoxyalkylene modified organopolysiloxane is represented by the formulae (A), (B), (C), and (D) shown below:

(A)

(B)

(C)

(D)

wherein R is an alkyl group having 1 to 3 carbon atoms or a phenyl group, R' is hydrogen or an alkyl group having 1 to 12 carbon atoms, p is an integer of 1 to 5, m is an integer of 5 to 100, n and x are integers of 1 to 50, t and y are integers of 0 to 50, the polyoxyalkylene modified organopolysiloxane contains 5 to 40% by weight of polyoxyalkylene groups in the molecule and said polyoxyalkylene modified organopolysiloxane having a molecular weight of 200 or more.

* * * * *